United States Patent
Wilhelmi et al.

(10) Patent No.: US 8,843,281 B2
(45) Date of Patent: Sep. 23, 2014

(54) SEED CHARACTERISTIC SENSOR

(75) Inventors: Matthew J. Wilhelmi, Parnell, IA (US); Courtney N. Achen, Iowa City, IA (US); Marvin L. Bachman, Marengo, IA (US)

(73) Assignee: Kinze Manufacturing, Inc., Williamsburg, IA (US)

( * ) Notice: Subject to any disclaimer, the term of this patent is extended or adjusted under 35 U.S.C. 154(b) by 185 days.

(21) Appl. No.: 13/234,483

(22) Filed: Sep. 16, 2011

(65) Prior Publication Data

US 2012/0067262 A1 Mar. 22, 2012

Related U.S. Application Data

(60) Provisional application No. 61/384,155, filed on Sep. 17, 2010.

(51) Int. Cl.
| | |
|---|---|
| G01F 1/05 | (2006.01) |
| G01F 1/07 | (2006.01) |
| G01F 1/08 | (2006.01) |
| G01F 1/20 | (2006.01) |
| G01V 8/10 | (2006.01) |
| A01C 7/10 | (2006.01) |

(52) U.S. Cl.
CPC .............. A01C 7/105 (2013.01); *Y10S 111/903* (2013.01); *Y10S 111/904* (2013.01)
USPC ............. 701/50; 111/200; 111/903; 111/904; 340/684; 250/222.2; 702/45; 702/49; 702/50

(58) Field of Classification Search
CPC ....................................................... A01C 7/105
USPC ........ 701/50; 702/28, 45, 48–50, 54, 82, 108, 702/128; 340/684; 250/222.2; 111/903, 111/904, 200
See application file for complete search history.

(56) References Cited

U.S. PATENT DOCUMENTS

| | | | |
|---|---|---|---|
| 8,504,310 B2 * | 8/2013 | Landphair et al. | ............. 702/45 |
| 2010/0116974 A1 * | 5/2010 | Liu et al. | .................... 250/222.2 |

* cited by examiner

*Primary Examiner* — Christopher J Novosad
(74) *Attorney, Agent, or Firm* — McKee, Voorhees & Sease

(57) ABSTRACT

Seed meters, agricultural planters, and methods of planting seed are provided. Such meters, planters, and methods may include a housing defining a chamber, a seed disc rotatably coupled to the housing and at least partially positioned within the chamber with the seed disc adapted to engage a seed, and a sensor for detecting a characteristic of the seed after the seed disengages the seed disc and before the seed exits the seed meter. The sensor may be coupled to a seed chute of the seed meter and may detect a wide variety of seed characteristics such as seed position within the seed chute, seed size, and seed shape. The seed characteristic may be used to adjust operation of the seed meters, agricultural planters, and methods. In some instances, the adjustment may be manual. In other instances, the adjustment may be automatic.

23 Claims, 8 Drawing Sheets

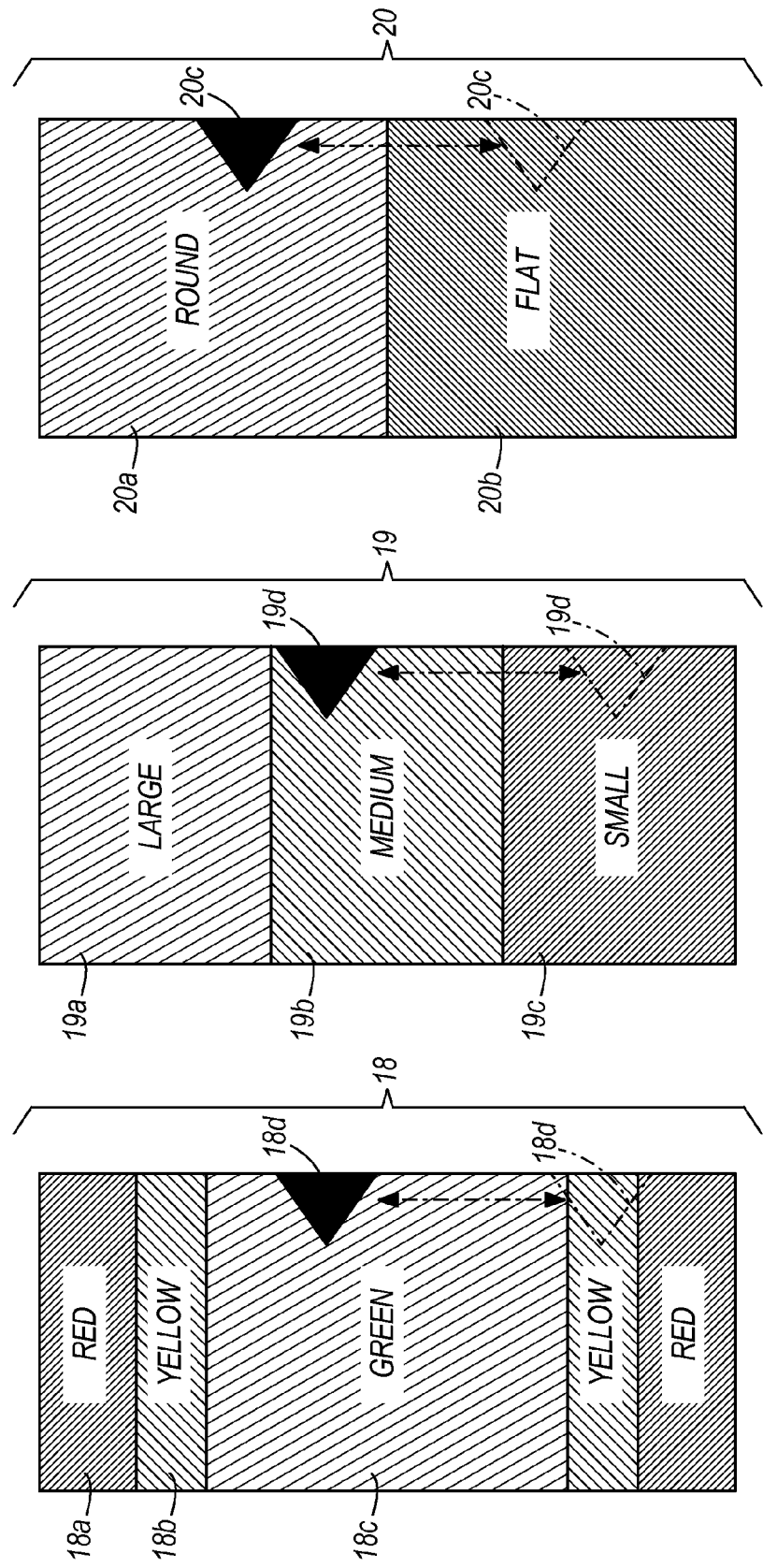

SEED CHARACTERISTIC SENSOR

RELATED APPLICATIONS

The present application claims the benefit of U.S. Provisional patent application No. 61/384,155, filed Sep. 17, 2010, the entire contents of which are incorporated herein by reference.

FIELD OF INVENTION

This invention relates generally to agricultural planters including a plurality of row units and seed meters and, more particularly, to consistent and accurate delivery of seeds to the ground.

BACKGROUND

Mechanical and vacuum seed meters are commonly used in agricultural planters in the planting of crops. A typical mechanical seed meter includes a housing and a rotating assembly within the housing having plural spaced "fingers" about its outer periphery. Each finger is adapted to receive an individual seed and hold that seed in place through mechanical spring force. Each seed is then sequentially released from its finger through an opening in a wall of the housing for the seed to exit into the seed tube where it falls, under gravity, to a furrow formed in the ground. In other mechanical meters, when seed exits the housing it is received by a belt which carries and drops the seed down the seed tube where it falls, under gravity, to the furrow. Still further, certain other types of mechanical seed meters use a rotatable drum or fluted roll instead of fingers to meter seeds. These meters also sequentially release the seed through an opening in the housing, allowing the seed to drop to the ground under the influence of gravity.

A typical vacuum seed meter includes a rotating seed disc having plural spaced apertures about its outer periphery. Each aperture is adapted to receive an individual seed which is maintained in position in the aperture on a first side of the seed disc by means of a vacuum applied to a second, opposed sided of the disc. Each seed is sequentially released from its aperture in the seed disc by interrupting the applied vacuum, allowing the seed to drop to the soil under the influence of gravity.

Vacuum seed meters have, to varying degrees, various operating limitations because of their design and the environment in which they operate. For example, a high vacuum must be maintained across the seed disc to securely maintain the seeds in position on the seed disc until they are released. The applied vacuum must be interrupted completely and very abruptly to allow for the consistent and accurate release of the individual seeds to ensure proper seed positioning and inter-seed spacing. Irregularities in seed position and inter-seed spacing result in poor plant development and reduced crop production. Once the vacuum source is removed from holding the seed to the disc it is only under the influence of gravity and friction from the disc it was recently adhered to.

After a seed is dropped by the mechanical or vacuum seed meter, the seed then travels to the ground down the seed tube. Any contact between the seed and the tube walls can influence seed velocity and affect inter seed spacing. Furthermore, with respect to vacuum seed meters, influence of the seed disc interface and tangential velocity of the seed at release will influence the fore and aft position of the seed traveling down the seed tube. Wide ranges in meter rotational speeds due to varying crop types and planting speeds in conjunction with a fixed vacuum removal point only broaden the magnitude of the fore and aft variance of the seed in the seed tube aforementioned above.

Present seed sensors are located in the seed tube, which is disposed between the seed meter and the soil, and such seed sensors may only provide feedback when the seed crosses a predetermined plane on its travel to the ground. Sensing within the seed tube introduces certain factors that can skew desired data associated with the sensed seed. For example, when the seed contacts an interior surface of the seed tube, the path of the seed is altered and may skew the desired data to be sensed by the sensor. This skewed data may result in false readings relating to, for example, inter-seed spacing, falsely counting skips or doubles, etc. Moreover, the data provided by these present seed sensors may only serve in calculating seed to seed spacing.

SUMMARY

In some examples, an apparatus, system and method are provided to facilitate more accurate placement of seeds in the soil during planting.

In other examples, more accurate feedback on seed meter performance is provided to allow meter settings to be changed to enhance seed placement by ensuring that the seed has an optimal, unimpeded path to the ground.

In further examples, an electronic control unit is provided and may receive feedback from a sensor and adjust meter settings automatically without operator input.

In still other examples, a sensor adapted to determine at least one seed characteristic such as, for example, a size, a shape, and/or a position of the seed is provided. Seed meter settings may be changed mechanically and/or electronically based on the seed characteristic in order to enhance seed placement.

In still further examples, a sensor is provided and may intercept a seed in the seed meter as it initiates travel from the seed meter to the soil. The sensor may include a plurality of sensing elements that allow a position of the seed to be calculated on a sensing plane. The plurality of sensing elements further allows for determining seed size and shape.

In yet other examples, a sensor is provided and includes at least on emitter and a plurality of receivers. The at least one emitter and the plurality of receivers cooperate to define a sensing plane. One coordinate location of a seed on the sensing plane may be calculated by determining which receivers are not receiving signals from the at least one emitter. Another coordinate of the seed location in the sensing plane is sensed by a distance measurement calculated by reflecting the sensing media back to at least one receiver on the same side as the at least one emitter. Another way of calculating the position is to have opposing emitters and receivers on opposing sides, with single emitters serving multiple receivers. Using this method, the location and number of receiver paths broken on each side can be triangulated and the position calculated. Yet another way of sensing the seed position is to have a perpendicular array of paired emitters and receivers on the X and Y axis. Using the signal from the blocked receivers in both the X and Y axis, the seed position can be calculated.

In yet further examples, seed size and shape may be determined. The seed size and shape may be deduced by how many blocked receiver paths in the array are broken in each direction, and the time it takes for the seed to pass through the sensing plane. Based on data from large samples, an algorithm may be used to determine the exact size based on an average of the length, width, and height of the seed.

In other examples, the information gathered in connection with the seed characteristics may be used to make manual adjustments to seed meter settings such as singulation, vacuum, and seed release point. This information may also be utilized in a closed loop control system to automatically adjust singulation, vacuum, and seed release point.

In further examples, a seed meter for an agricultural planter is provided and includes a housing defining a chamber, a seed disc rotatably coupled to the housing and at least partially positioned within the chamber, the seed disc is adapted to engage a seed, and a sensor for detecting a characteristic of the seed after the seed disengages the seed disc and before the seed exits the seed meter.

In yet other examples, an agricultural planter is provided and includes a seed meter including a housing defining a chamber, a seed disc rotatably coupled to the housing and at least partially positioned within the chamber, wherein the seed disc is adapted to be engaged by a seed, and a seed chute. The agricultural planter also including a sensor for detecting a characteristic of the seed after the seed disengages the seed disc and before the seed exits the seed meter, and a seed tube formed separately from the seed chute and at least partially aligned with the seed chute to receive the seed after the seed exits the seed chute, wherein the seed tube communicates the seed to a furrow.

In yet further examples, a method of planting seed with an agricultural planter is provided and includes providing a seed meter for singulating seed therefrom, the seed meter including a seed disc engageable by seed and a seed chute defining a cavity therein, providing a sensor, dispensing a first seed from the seed disc and into the cavity of the seed chute, determining a characteristic of the first seed with the sensor while the first seed is positioned within the cavity of the seed chute, communicating information associated with the characteristic of the first seed to an electronic control unit, and adjusting dispensing of a second seed from the seed meter based on the communicated information associated with the characteristic of the first seed.

BRIEF DESCRIPTION OF THE DRAWINGS

FIG. 9 is an exemplary image displayable on an operator interface;

FIG. 10 is another exemplary image displayable on an operator interface;

FIG. 11 is a further exemplary image displayable on an operator interface;

Figure 1:
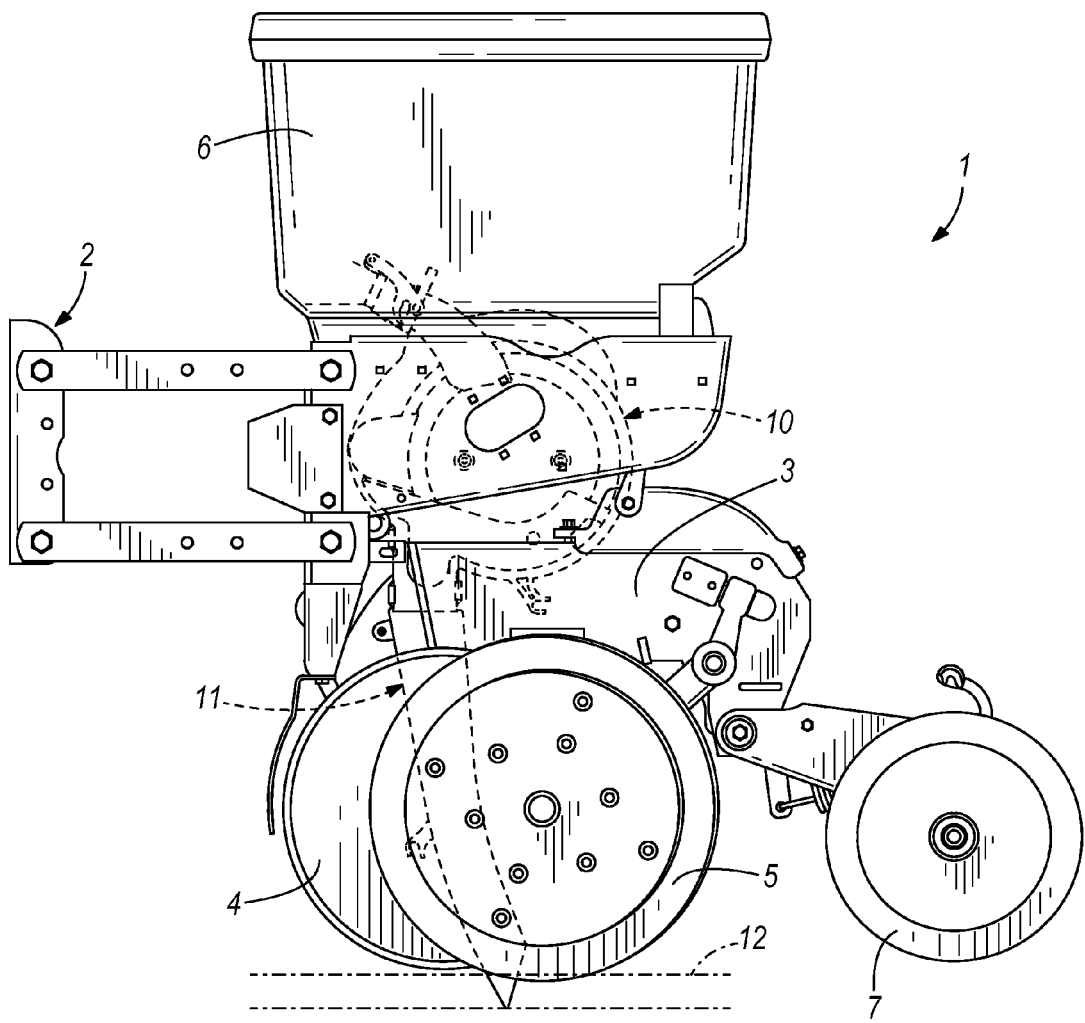
FIG. 1 is a side view of an exemplary row unit of a planter, the row unit including an exemplary seed characteristic sensor.

Before any independent features and embodiments of the invention are explained in detail, it is to be understood that the invention is not limited in its application to the details of the construction and the arrangement of the components set forth in the following description or illustrated in the drawings. The invention is capable of other embodiments and of being practiced or of being carried out in various ways. Also, it is understood that the phraseology and terminology used herein is for the purpose of description and should not be regarded as limiting.

DETAILED DESCRIPTION

Figure 2:
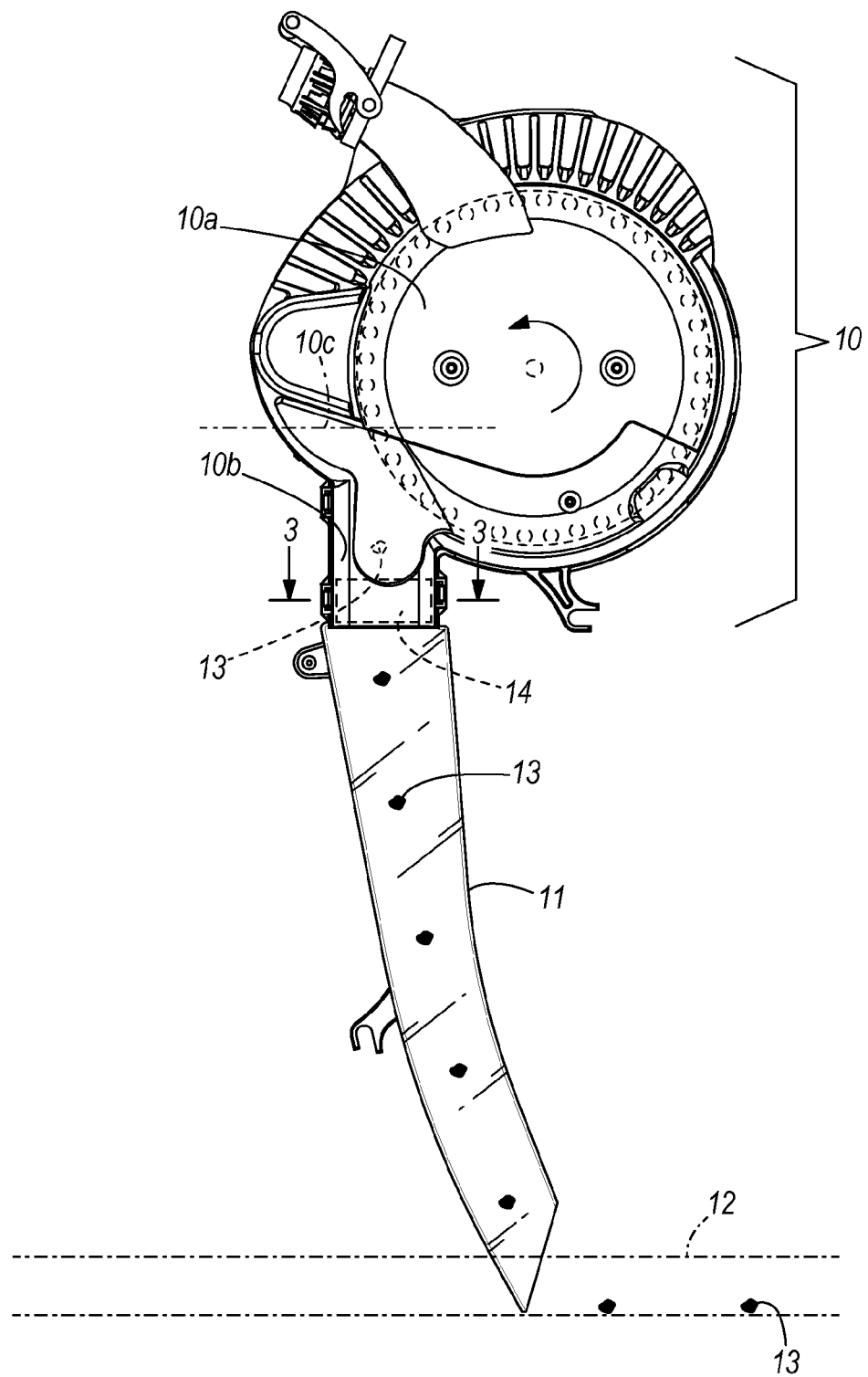
FIG. 2 is side view of a portion of the row unit shown in FIG. 1, the illustrated portion of the row unit including an exemplary seed meter, an exemplary seed tube, and an exemplary seed characteristic sensor.

With reference to FIGS. 1 and 2, an exemplary row unit 1 of an agricultural planter is illustrated. The row unit 1 may be coupled to a frame or toolbar (not shown) of a tractor by a coupling 2. The row unit 1 includes a frame 3 coupled to the coupling 2, a pair of flat circular disc blades 4 coupled to the frame 3 to open a seed trench or furrow in the ground, a pair of depth gauge wheels 5 coupled to the frame 3 and located adjacent to and slightly to a rear of the blades 4, a seed meter 10 which "singulates" seed 13 from a seed hopper 6 and drops the seed 13 one at a time from the seed meter 10, and a seed tube 11 formed separately from the seed chute 10b, at least partially aligned with the seed chute 10b to receive the seed 13 after exiting the seed chute 10b, and facilitates deposit of the seed 13 into the furrow formed by the twin disc opener blades 4. The row unit 1 also includes a seed characteristic sensor 14 for sensing characteristics of the seed 13 and a pair of spaced apart closing wheels 7 coupled to the frame 3 and positioned to follow after the planted seed 13 for breaking down the furrow side walls on either side of the furrow and cover the seed 13, close the furrow, and firm the soil over the covered seed 13. The gauge wheels 5 determine, at least in part, the depth of the furrow formed by the opener blades 4. The seed meter 10 may be any type of seed meter 10 such as, for example, a mechanical seed meter, a vacuum seed meter, etc., and be within the intended spirit and scope of the present invention. The following description and associated figures relate to a vacuum seed meter. However, such description and figures of the vacuum seed meter are not intended to be limiting upon the present invention.

Referring to FIG. 2, a portion of the row unit 1 is illustrated and includes the seed meter 10, which is comprised of a seed disc 10a, a seed chute 10b, and the seed characteristic sensor 14. Seed 13 is held to the seed disc 10a by a conventional vacuum source. The seed 13 then rotates to a point where the vacuum source is removed 10c, thereby causing the seed 13 to leave the disc and enter the seed chute 10b. As the seed 13 passes down the seed chute 10b of the seed meter 10, the seed 13 is intercepted by the seed characteristic sensor 14, which can be unitary with the seed meter 10. After passing the seed characteristic sensor 14 and exiting the seed chute 10b, the seed 13 then enters the seed tube 11 and is delivered to the ground 12. The seed chute 10b has first and second opposing side walls 50, 51 and third and fourth opposing side walls 52, 53, together defining a cavity 54 in the seed chute 10b for passage of a seed 13 from the seed meter 10 to the seed tube 11. In one exemplary embodiment, the seed characteristic sensor 14 may be positioned adjacent an outside or exterior 55 of any of the side walls 50-53 of the seed chute 10b. The seed characteristic sensor 14 detects at least one seed characteristic for each seed 13. Such characteristics may include, for example, seed position, seed size, seed shape, etc. Positioning the seed characteristic sensor 14 adjacent to the seed chute 10b allows the seed characteristic sensor 14 to detect the seed characteristic before movement of the seed is affected by other factors. Such factors may include, for example, engagement of the seed with one of the side walls 50-53, etc.

The seed characteristic sensor may be a wide variety of types of sensors such as, for example, infrared sensors, LED sensors, lasers, visible light, etc. The sensors illustrated and described herein are for exemplary purposes only and are not intended to be limiting upon the present invention. Rather, any type of sensor may be used with the present invention.

It should be understood that the seed characteristic sensor 14 may be coupled to the seed chute 10b in a variety of manners and in a variety of positions, but ultimately be able to determine at least one seed characteristic. For example, the seed characteristic sensor 14 may be clipped, bolted, fastened, tied (e.g., with plastic ties), adhered, unitarily formed with as one-piece, etc. to the seed chute 10b. In some exemplary embodiments, one or more of the side walls 50-53 may be made of a transparent or translucent material to allow the seed characteristic sensor 14 to operate through the one or more side walls 50-53 of the seed chute 10b (see e.g., FIG. 3). In other exemplary embodiments, an opening may be defined in one or more of the side walls 50-53 and the seed characteristic sensor 14 may be at least partially aligned with and/or positioned within the opening to sense at least one seed characteristic (see e.g., FIG. 7).

It should also be understood that the seed sensor may be coupled to other portions of the seed meter or to other portions of the row unit 1 and be within the intended spirit and scope of the present invention.

Figure 3:
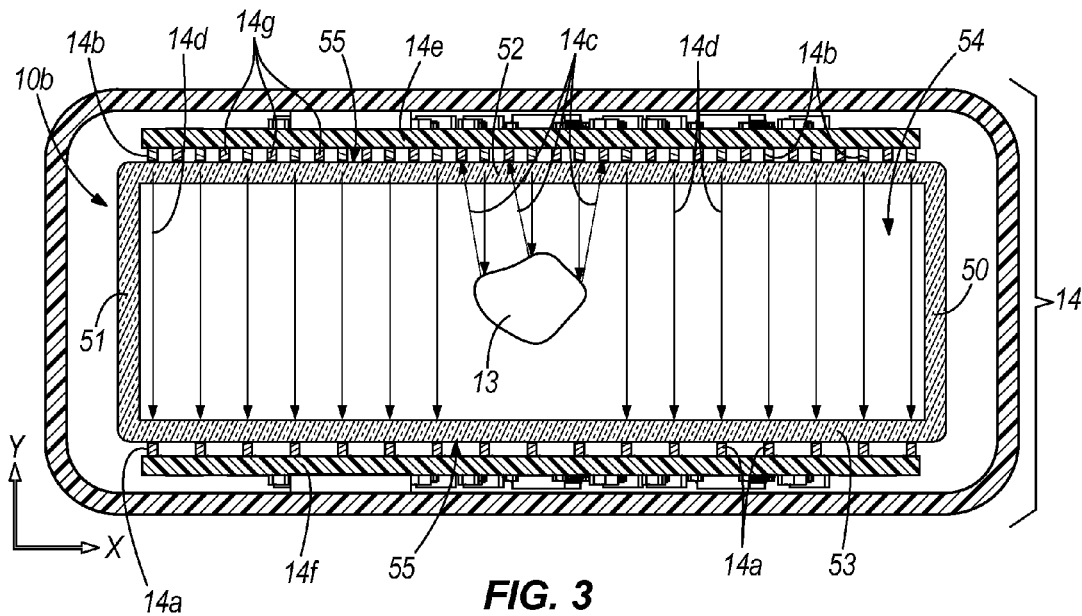
FIG. 3 is a cross-sectional view taken along line 3-3 in FIG. 2.

With reference to FIG. 3, an exemplary embodiment of the seed characteristic sensor 14 is illustrated and includes a plurality of substantially coplanar emitters 14b, a first plurality of substantially coplanar receivers 14a, and a second plurality of substantially coplanar receivers 14g. In some exemplary embodiments, the emitters 14b, the receivers 14a, and the receivers 14g are all substantially coplanar with each other. The emitters 14b and receivers 14g are coupled to circuit board 14e and the receivers 14a are coupled to circuit board 14f. When the seed 13 travels down the seed chute 10b, it breaches at least one of the beams 14d emitted by the emitters 14b. The X position of the seed 13 can be calculated by determining which beams 14d are blocked by the seed 13. As the seed 13 breaks one or more of the beams 14d emitted by the emitters 14b, the broken beams 14c reflect back in the direction of the emitters 14b. The reflected back beams 14c are sensed by the receivers 14g positioned on the same side of the chute 10b as the emitters 14b. The position in the Y direction may be calculated by a measure of the time it takes for the reflected back broken beams 14c to be sensed by the receivers 14g. In this illustrated exemplary embodiment, the side walls 50-53 of the chute 10b are made of a transparent or translucent material to allow the emitters 14b and receivers 14a, 14g to be positioned externally of the cavity 54 and operate through the side walls 50-53 to sense seed characteristics. By positioning the seed characteristic sensor 14 externally of the cavity 54, the seed characteristic sensor 14 is not exposed to the environment within the cavity 54. Exposure to such environment may negatively affect the performance of the seed characteristic sensor 14.

Figure 4:
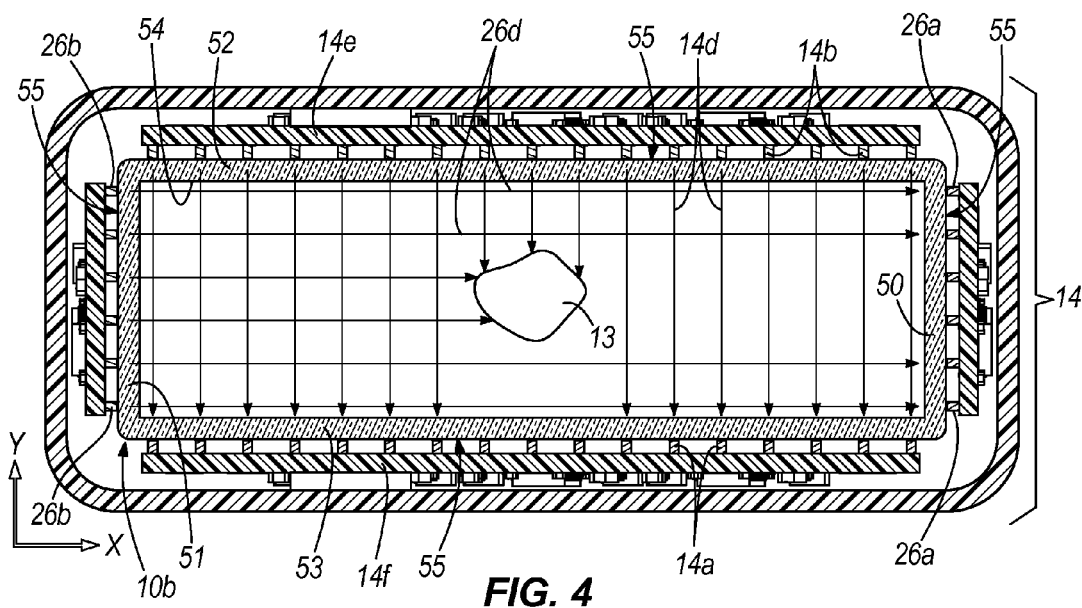
FIG. 4 is a cross-sectional view taken along a similar reference plane as FIG. 3 showing another exemplary seed characteristic sensor.

With reference to FIG. 4, another exemplary embodiment of a seed characteristic sensor 26 is illustrated and the sensor 26 includes a perpendicular set of coplanar emitters 26b and receivers 26a that will calculate the seed's 13 position in the X and Y dimensions. In this illustrated exemplary embodiment, the X dimension is calculated in a similar manner to that described above in connection with FIG. 3. That is, the emitters 14b and receivers 14a cooperate to determine which beams 14d are blocked by the seed 13. The Y dimension in this illustrated exemplary embodiment may be calculated with emitters 26b and receivers 26a. The emitters 26b emit beams 26d and the receivers 26a are capable of receiving the beams 26d. As the seed 13 passes through the beams 26d, at least one of the beams 26d is blocked. Thus, the emitters 26b and receivers 26a cooperate to determine which beams 26d are blocked by the seed 13, thereby calculating the Y dimension of the seed 13. By determining the number of emitter beams 14d that are blocked, the size of the seed in the X axis can be calculated. Seed size in the Y axis may be determined by the number of emitter beams 26d that are blocked. The final dimension of seed size may be calculated using the time it takes the seed 13 to pass through the seed characteristic sensor's 14 sensing plane.

Figure 5:
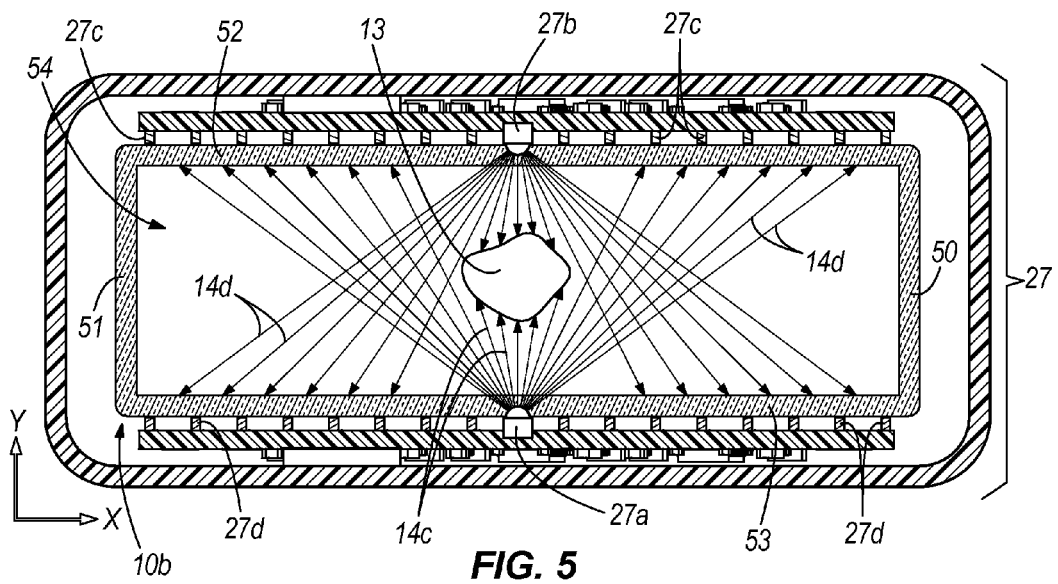
FIG. 5 is a cross-sectional view taken along a similar reference plane as FIG. 3 showing a further exemplary seed characteristic sensor.

Referring now to FIG. 5, yet another exemplary embodiment of a seed characteristic sensor 27 is shown and includes single source emitters 27a and 27b that are located on opposite sides of the chute 10b and two sets of receivers 27c and 27d, one set associated with each emitter 27a and 27b. Each emitter 27a or 27b provides the sensing media for its respective set of receivers 27c and 27d located on the opposite side of the chute 10b. The position of the seed 13 in both the X and Y locations can be triangulated by determining the number of receivers 27c and 27d blocked on each side of the chute 10b.

Figure 6:
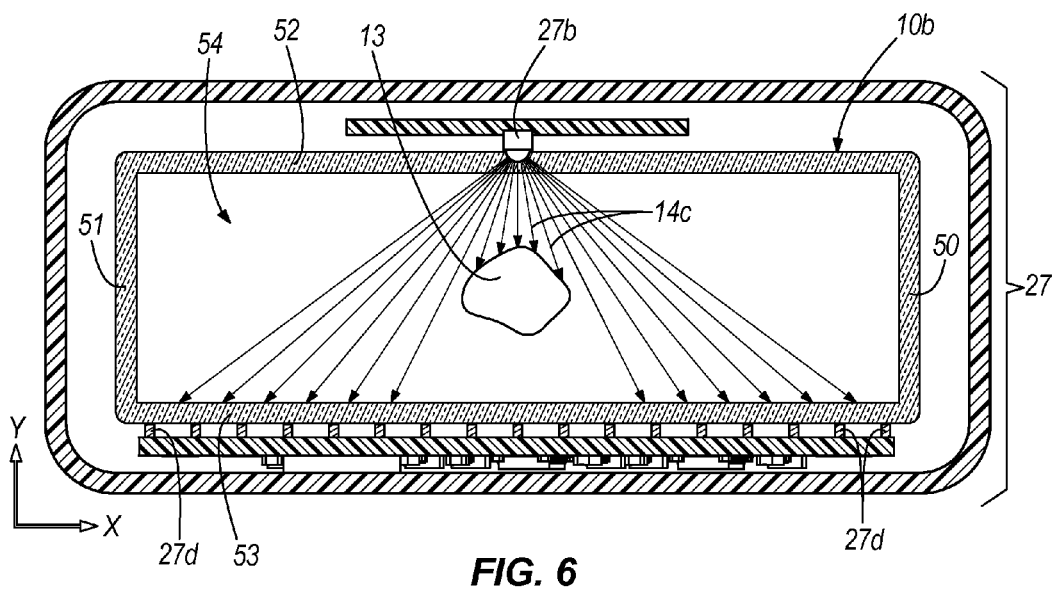
FIG. 6 is a cross-sectional view taken along a similar reference plane as FIG. 3 showing yet another exemplary seed characteristic sensor.

Referring now to FIG. 6, yet another exemplary embodiment is illustrated and includes one single source emitter 27b and one set of receivers 27d for receiving emitter beams 14d from the emitter 27b. The characteristics of the seed 13 such as, for example, position and size, may be determined in a similar manner to that described in connection with FIG. 5.

Figure 7:
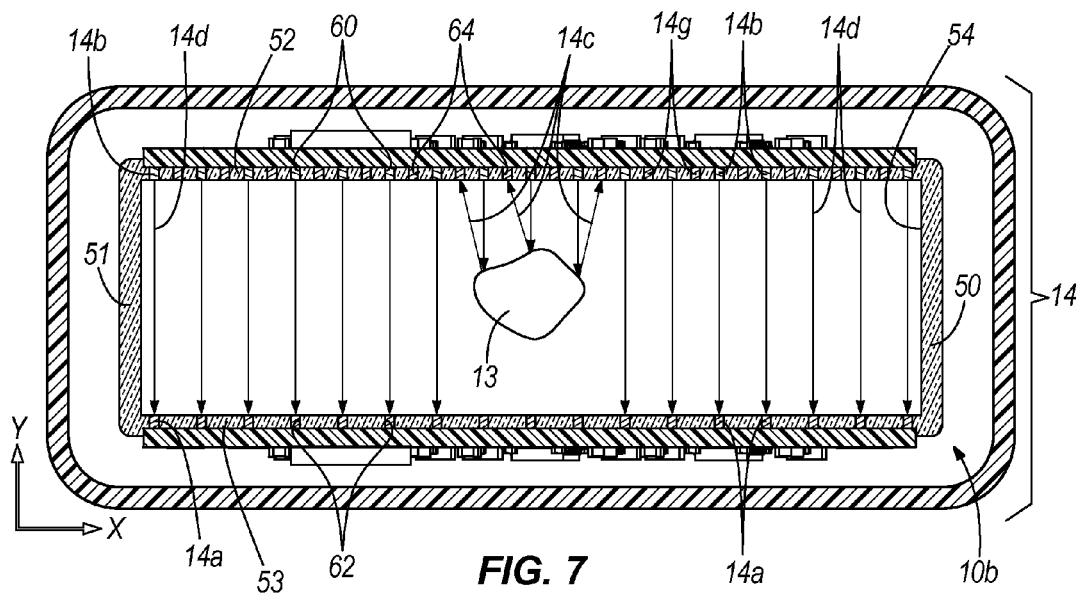
FIG. 7 is a cross-sectional view taken along a similar reference plane as FIG. 3 showing yet a further exemplary seed characteristic sensor.

With reference to FIG. 7, openings 60, 62, 64 are defined in each of the side walls 52, 53. The emitters 14b are positioned in openings 60 defined in side wall 52, the receivers 14a are positioned in openings 62 defined in side wall 53, and receivers 14g are positioned in openings 64 defined in side wall 52. In this exemplary embodiment, the emitted beams 14d from the emitters 14b do not pass through any of the side walls 50-53 of the chute 10b due to the openings 60, 62, 64. It should be understood that any number of the side walls 50-53 of the chute 10b may have openings defined therein for receiving emitters or receivers and be within the intended spirit and scope of the present invention. For example, the embodiment illustrated in FIG. 7 includes openings 60, 62, 64 defined in side walls 52 and 53. Alternatively, all four side walls 50-53 of the chute 10b may have openings defined therein to receive emitters and receivers. Such an alternative embodiment may be appropriate to accommodate an emitter and receiver configuration illustrated in FIG. 4.

Figure 8:
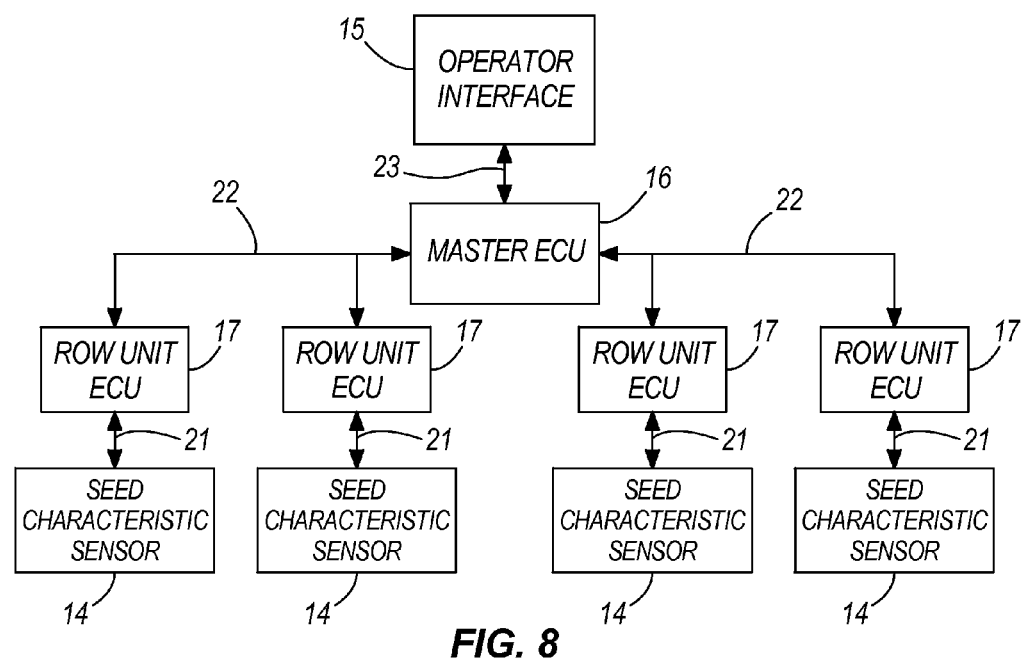
FIG. 8 is an exemplary system diagram.

Referring now to FIG. 8, an exemplary system or network is illustrated. Information associated with seed characteristics may be sent from the seed characteristic sensor 14 via a communication protocol 21 to a row unit electronic control unit 17. In the illustrated exemplary embodiment, one row unit ECU 17 is associated with each row unit 1 and each seed characteristic sensor 14 communicates with its own row unit ECU 17. A plurality of seed meters 10 including the seed characteristic sensors 14 can then be connected to a master electronic control unit 16 via a communication protocol 22. The master ECU 16 then feeds the signal to an operator interface 15 using an implement communication bus 23. The operator interface 15 may be a wide variety of devices capable of displaying information such as text and images to an operator. For example, the operator interface may be a display, a monitor, etc.

FIG. 9, FIG. 10, and FIG. 11 relate to the feedback provided to the operator from the seed characteristic sensor 14, through the system or network described in connection with FIG. 8. It should be understood that the exemplary embodiments illustrated in FIGS. 9-11 of displayed feedback are one manner of many possible manners of displaying feedback and all such manners are intended to be within the spirit and scope of the present invention.

FIG. 9 shows the operator feedback for a position of the seed 13 in the seed chute 10b. In the illustrated exemplary embodiment, the operator feedback for position 18 consists of three zones in which the seed 13 can fall through the seed chute 10b. These three zones are green 18c, yellow 18b, and red 18a. The indicator 18d signifies which range the seed 13 is in and is moveable between zones depending on the position of the seed 13. Green 18c represents to the operator that spacing average is being optimized, while yellow 18b and red 18a signifies that adjustments might need to be made. In other embodiments of this invention other colors may be used. In still other exemplary embodiments, any number of zones having any sized increments may be used. An audio or visual warning signal may be triggered if seed spacing is not optimal or if the system is operating erratically.

FIG. 10 is a depiction of seed size presented to the operator on the operator interface 15. FIG. 10 represents the seed size 19 on the operator interface 15 which is broken into three categories large 19a, medium 19b, and small 19c. The indicator 19d dictates to the operator where the seed 13 is in the range. This information is further used to make manual adjustments to the seed meter 10 to increase performance of the meter 10 for the size of the seed 13 being planted. It should be understood that the size characterizations and categories described above (i.e., small, medium, and large) and illustrated in FIG. 10 are only exemplary size characterizations and categories, and the invention is capable of having different size characterizations and categories, and being within the intended spirit and scope of the present invention. It should also be understood that a depiction displayed on the operator interface 15 relating to size of the seed may include any number of categories or size characterizations and be within the intended spirit and scope of the present invention. The illustrated exemplary embodiment includes three categories or size characterizations. Other exemplary embodiments may include any number of categories or size characterizations.

Shape of the seed is represented by the shape output 20 on the operator interface 15 which can be seen in FIG. 11. In the illustrated exemplary embodiment, there are two designations for seed shape, round 20a and flat 20b. The shape is communicated to the operator via the indicator 20c. Information about seed shape will be used by the operator to make seed meter 10 adjustments to increase spacing accuracy. It should be understood that the shape designations or characterizations described above (i.e., round and flat) and illustrated in FIG. 11 are only exemplary shape designations and characterizations and the invention is capable of having different shape designations and characterizations and be within the intended spirit and scope of the present invention. It should also be understood that a depiction displayed on the operator interface 15 relating to shape of the seed may include any number of designations or shape characterizations and be within the intended spirit and scope of the present invention. The illustrated exemplary embodiment includes two designations or shape characterizations. Other exemplary embodiments may include any number of designations or shape characterizations.

Figure 12:
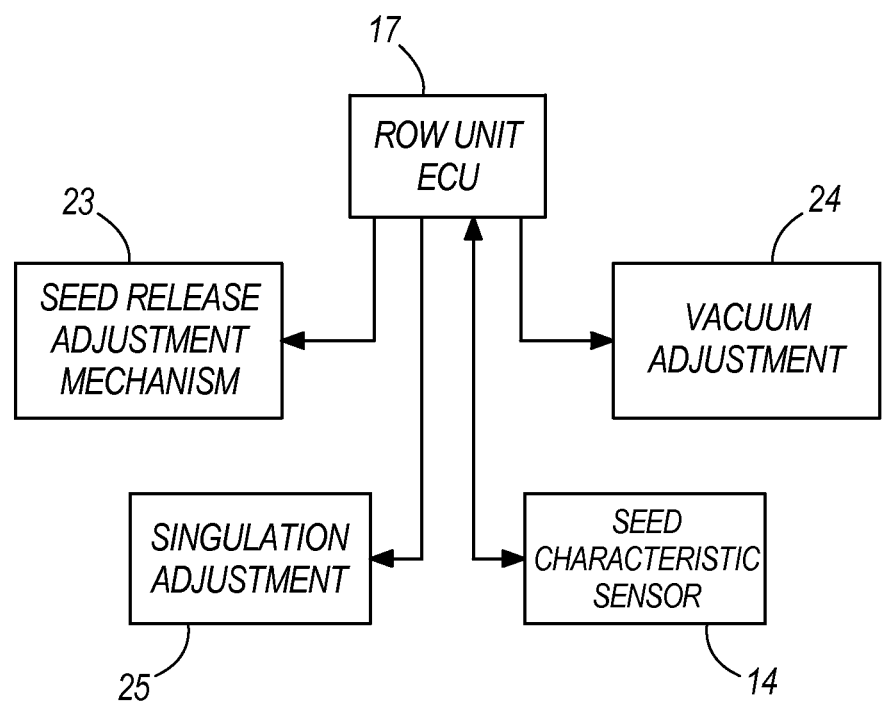
FIG. 12 is another system diagram.

FIG. 12 relates to a closed loop control of adjustments based on information from the seed characteristic sensor 14 in lieu of manual adjustments. Data associated with one or more seed characteristics such as, for example, seed position, seed size, and seed shape is received by the row unit ECU 17 from the seed characteristic sensor 14 and is used by said row unit ECU 17 to determine what adjustments need to be made to the seed meter 10 to improve spacing accuracy.

Data associated with the one or more seed characteristics may be used to make adjustments electronically to the seed release adjustment mechanism 23 to ensure that the seed 13 is consistently being dropped as close to a middle of the seed chute 10b as desired. The seed release adjustment mechanism 23 may also be adjusted proportionally to implement ground speed which will be available through the main communication protocol 22. All adjustments are made electronically and independent of the operator.

Some seed characteristics such as, for example, seed size and seed shape may dictate adjustments to the vacuum 24 and singulation 25. The row unit ECU 17 may make determinations on adjustments to vacuum 24 and singulation 25 based on seed size, shape, and meter speed and adjust them electronically without input from the operator.

Figure 13:
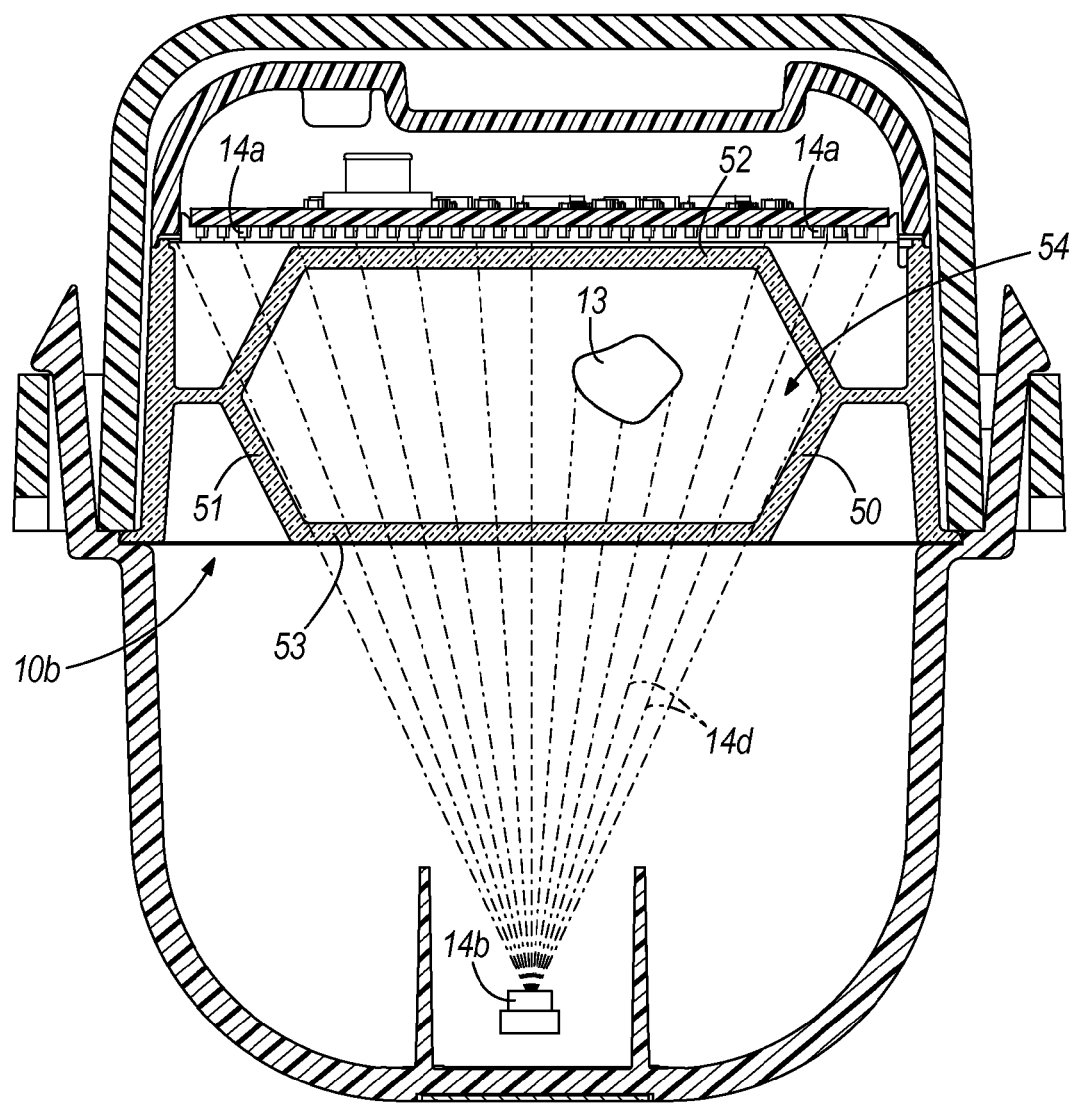
FIG. 13 is a cross-sectional view taken along a similar reference plane as FIG. 3 showing still another exemplary seed characteristic sensor.

Referring now to FIG. 13, still another exemplary embodiment is illustrated and includes a single emitter 14b and a plurality of receivers 14a for receiving beams 14d emitted by the emitter 14b. The walls 50-53 of the seed chute 10b are transparent or translucent to allow the beams 14d to pass through the walls 50-53 and be received by the receivers 14a. As a seed 13 passes through the seed chute 10b, the seed will block a portion of the beams 14d, thereby indicating to the seed characteristic sensor 14 and the row unit ECU 17 a characteristic of the seed 13. In this illustrated exemplary embodiment, the walls 50-53 of the seed chute 10b have a different configuration than the walls 50-53 of the seed chute 10b in other illustrated exemplary embodiments. In the illustrated exemplary embodiment, the opposing walls 50 and 51 are not linear, but instead are each comprised of two intersecting angled portions, thereby providing the chute 10b with an overall hexagonal cross-sectional shape.

It should be understood that while the opposing walls 50-53 may have a variety of shapes and configurations that may not be substantially linear and parallel with each other, the two walls 50 and 51 and the two walls 52 and 53 may remain opposing to each other on opposite sides of the cavity 54 no matter the shape and configuration of the walls 50-53.

It should also be understood that the walls of the seed chute may have a wide variety of shapes and all of such possible shapes are intended to be within the spirit and scope of the present invention.

It should further be understood that the features of any of the exemplary embodiments illustrated and described herein may be incorporated into any of the other exemplary embodiments illustrated and described herein in any combination and without any limitation.

The foregoing description has been presented for purposes of illustration and description, and is not intended to be exhaustive or to limit the invention to the precise form disclosed. The descriptions were selected to explain the principles of the invention and their practical application to enable others skilled in the art to utilize the invention in various embodiments and various modifications as are suited to the particular use contemplated. Although particular constructions of the present invention have been shown and described, other alternative constructions will be apparent to those skilled in the art and are within the intended scope of the present invention.

We claim:

1. A seed meter for an agricultural planter, the seed meter comprising:
a housing defining a chamber;
a seed disc rotatably coupled to the housing and at least partially positioned within the chamber, wherein the seed disc is adapted to engage a seed;
a seed chute extending from the housing and configured to direct seed that has been released from the seed disc towards the ground; and
a sensor positioned at least partially within the seed chute for detecting a characteristic of the seed after the seed disengages the seed disc and before the seed exits the seed meter.

2. The seed meter of claim 1, further comprising a seed tube formed separately of the seed chute, wherein the sensor detects the characteristic of the seed before the seed enters the seed tube.

3. The seed meter of claim 2, wherein at least a portion of the seed chute is transparent and the sensor is positioned externally of the seed chute and adjacent to the transparent portion of the seed chute to detect the characteristic of the seed through the transparent portion of the seed chute.

4. The seed meter of claim 2, wherein the characteristic of the seed is one of seed position relative to the seed chute, seed size, and seed shape.

5. The seed meter of claim 2, wherein the sensor includes at least one emitter and at least one receiver, and wherein the at least one emitter and the at least one receiver are positioned adjacent the seed chute and cooperate to detect the characteristic of the seed when the seed is at least partially within the seed chute.

6. The seed meter of claim 5, wherein the characteristic of the seed is one of seed position relative to the seed chute, seed size, and seed shape.

7. The seed meter of claim 5, wherein the seed chute includes first and third opposing side walls and second and fourth opposing side walls, the walls together defining an interior of the seed chute, and wherein at least a portion of each of the first and third opposing walls is transparent and the emitter is positioned adjacent an exterior of the transparent portion of the first wall and the receiver is positioned adjacent an exterior of the transparent portion of the third wall.

8. The seed meter of claim 7, wherein the sensor includes a plurality of receivers, and wherein the plurality of receivers are positioned adjacent the exterior of the transparent portion of the third wall.

9. The seed meter of claim 8, wherein the plurality of receivers are coplanar.

10. The seed meter of claim 7, wherein at least a portion of each of the second and fourth opposing walls is transparent, and wherein the sensor includes a second emitter positioned adjacent an exterior of the transparent portion of the second wall and includes a second receiver positioned adjacent an exterior of the transparent portion of the fourth wall.

11. The seed meter of claim 10, wherein the sensor includes a plurality of receivers, and wherein the plurality of receivers are positioned adjacent the exterior of the transparent portion of the fourth wall.

12. The seed meter of claim 11, wherein the plurality of receivers are coplanar.

13. An agricultural planter comprising:
a seed meter including a housing defining a chamber, a seed disc rotatably coupled to the housing and at least partially positioned within the chamber, wherein the seed disc is adapted to be engaged by a seed;
a seed chute extending from the housing and configured to direct seed that has been released from the seed disc towards the ground;
a sensor positioned within at least a portion of the seed chute for detecting a characteristic of the seed after the seed disengages the seed disc and before the seed exits the seed meter; and
a seed tube formed separately from the seed chute and at least partially aligned with the seed chute to receive the seed after the seed exits the seed chute, wherein the seed tube communicates the seed to a furrow.

14. The agricultural planter of claim 13, wherein the sensor includes at least one emitter and at least one receiver, and wherein the at least one emitter and the at least one receiver are positioned adjacent the seed chute and cooperate to detect the characteristic of the seed when the seed is at least partially positioned within the seed chute.

15. The agricultural planter of claim 14, wherein the characteristic of the seed is one of seed position relative to the seed chute, seed size, and seed shape.

16. The agricultural planter of claim 14, wherein the seed chute includes first and third opposing side walls and second and fourth opposing side walls, the walls together defining an interior of the seed chute, and wherein at least a portion of each of the first and third opposing walls is transparent and the at least one emitter is positioned adjacent an exterior of the transparent portion of the first wall and the at least one receiver is positioned adjacent an exterior of the transparent portion of the third wall.

17. The agricultural planter of claim 16, wherein the sensor includes a plurality of receivers positioned adjacent the exterior of the transparent portion of the third wall.

18. The agricultural planter of claim 17, wherein the plurality of receivers are coplanar.

19. A method of planting seed with an agricultural planter, the method comprising:
providing a seed meter for singulating seed therefrom, the seed meter including a seed disc engageable by seed;
providing a sensor;
dispensing a first seed from the seed disc and towards a seed chute and a separate seed tube;
determining a characteristic of the first seed with the sensor after the first seed is dispensed from the seed disc as it passes through the seed chute and before the first seed enters the seed tube;
communicating information associated with the characteristic of the first seed to an electronic control unit; and
adjusting dispensing of a second seed from the seed meter based on the communicated information associated with the characteristic of the first seed.

20. The method of claim 19, further comprising
displaying at least one of text and an image on an operator interface, wherein the at least one of text and an image is associated with the communicated information associated with the characteristic of the first seed; and
wherein the step of adjusting further comprises manually adjusting dispensing of a second seed from the seed meter based on the communicated information associated with the characteristic of the first seed.

21. The method of claim 19, wherein the step of adjusting further comprises automatically adjusting, without operator interaction, dispensing of a second seed from the seed meter based on the communicated information associated with the characteristic of the first seed.

22. The method of claim 19, wherein the seed chute further includes a cavity therein, and wherein determining a characteristic of the first seed further comprises determining the characteristic of the first seed with the sensor while the first seed is in the cavity of the seed chute.

23. The method of claim 22, wherein the step of providing a sensor further comprises providing a sensor including an emitter positioned on a first side of the seed chute cavity and a plurality of receivers positioned on a second side of the seed chute cavity opposite the first side, and wherein the step of determining a characteristic of the seed further comprises emitting a sensing media from the emitter across the cavity towards the plurality of receivers, blocking at least a portion of the sensing media with the first seed as the first seed passes through the sensing media, and determining, with the plurality of receivers, at least one of the portion of the sensing media blocked by the first seed with the plurality of receivers, and a quantity of time the first seed blocked the portion of the sensing media.

* * * * *